(12) United States Patent
Deboeuf et al.

(10) Patent No.: US 11,337,764 B2
(45) Date of Patent: May 24, 2022

(54) ROBOTIZED MODULE FOR GUIDING AN ELONGATE FLEXIBLE MEDICAL DEVICE

(71) Applicant: ROBOCATH, Rouen (FR)

(72) Inventors: Sébastien Deboeuf, Bonsecours (FR); Fabien Destrebecq, Bourgtheroulde (FR); Bruno Fournier, Saint Ouen (FR); Philippe Bencteux, Saint Martin du Vivier (FR)

(73) Assignee: ROBOCATH, Rouen (FR)

( * ) Notice: Subject to any disclaimer, the term of this patent is extended or adjusted under 35 U.S.C. 154(b) by 1099 days.

(21) Appl. No.: 15/317,020

(22) PCT Filed: Jun. 12, 2015

(86) PCT No.: PCT/FR2015/051562
§ 371 (c)(1),
(2) Date: Dec. 7, 2016

(87) PCT Pub. No.: WO2015/189529
PCT Pub. Date: Dec. 17, 2015

(65) Prior Publication Data
US 2017/0151024 A1  Jun. 1, 2017

(30) Foreign Application Priority Data
Jun. 12, 2014 (FR) .................................. 14 55330

(51) Int. Cl.
*A61B 34/30* (2016.01)
*A61B 46/10* (2016.01)
(Continued)

(52) U.S. Cl.
CPC .............. *A61B 34/30* (2016.02); *A61B 46/10* (2016.02); *A61B 50/00* (2016.02);
(Continued)

(58) Field of Classification Search
CPC ......... A61B 46/00; A61B 46/10; A61B 46/23; A61B 2046/234; A61B 34/30;
(Continued)

(56) References Cited

U.S. PATENT DOCUMENTS

| 7,927,310 B2 | 4/2011 | Bencteux |
| 2007/0185404 A1 | 8/2007 | Hauck et al. |

(Continued)

FOREIGN PATENT DOCUMENTS

| EP | 2567670 A1 | 3/2013 |
| WO | 2008115151 A1 | 9/2008 |
| WO | WO 2014/005689 A2 | 1/2014 |

OTHER PUBLICATIONS

International Search Report Application No. PCT/FR2015/051562 reported on Sep. 23, 2015.
(Continued)

*Primary Examiner* — Alireza Nia
*Assistant Examiner* — Kevin S Albers
(74) *Attorney, Agent, or Firm* — von Briesen & Roper, s.c.

(57) ABSTRACT

The invention concerns a cassette comprising a sterile barrier. The sterile barrier comprises attachment brackets each attached to a drive member for driving an elongate flexible medical device, and flexible portions between two adjacent attachment brackets. The flexible portions are connected to the attachment brackets. The drive surfaces of the attachment brackets come into contact with the elongate flexible medical device.

25 Claims, 11 Drawing Sheets

(51) Int. Cl.
*A61B 50/00* (2016.01)
*A61M 25/01* (2006.01)

(52) U.S. Cl.
CPC .... *A61M 25/0113* (2013.01); *A61B 2034/301* (2016.02); *A61B 2050/005* (2016.02); *A61M 2025/0166* (2013.01)

(58) Field of Classification Search
CPC ........ A61B 2034/301; A61B 2034/302; A61B 2034/303; A61B 2034/304; A61B 2034/305; A61B 2034/306; A61B 50/00; A61M 2025/0166; A61M 25/0113
USPC ......................................................... 128/852
See application file for complete search history.

(56) References Cited

U.S. PATENT DOCUMENTS

| | | | | |
|---|---|---|---|---|
| 2007/0239172 A1* | 10/2007 | Lee | ........................ | A61B 34/37 606/130 |
| 2009/0082722 A1 | 3/2009 | Pryor | | |
| 2010/0170519 A1* | 7/2010 | Romo | .................... | A61B 34/30 128/852 |
| 2012/0179167 A1* | 7/2012 | Wenderow | ............. | A61B 34/30 606/130 |
| 2012/0245595 A1 | 9/2012 | Kesavadas et al. | | |
| 2013/0085389 A1 | 4/2013 | Tsang et al. | | |
| 2013/0172713 A1 | 7/2013 | Kirschenman | | |
| 2013/0172738 A1 | 7/2013 | Bencteux et al. | | |
| 2015/0173840 A1* | 6/2015 | Lohmeier | .............. | A61B 34/76 606/130 |
| 2018/0125589 A1 | 5/2018 | Murphy et al. | | |

OTHER PUBLICATIONS

Notice of Reasons for Rejection related to Japanese Application No. 2016-572660; dated Mar. 14, 2019.
Decision of Rejection related to Japanese Application No. 2016-572660; dated Feb. 7, 2020.
First Chinese Office Action related to Chinese Application No. 201580036079.6; dated Oct. 25, 2018.

* cited by examiner

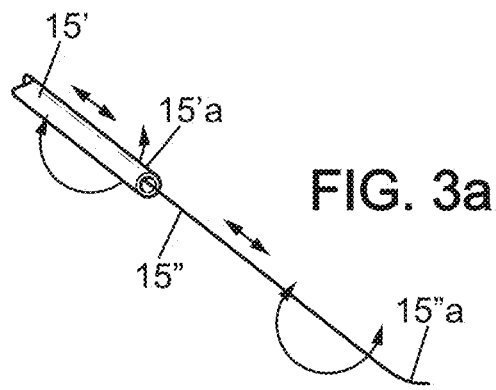
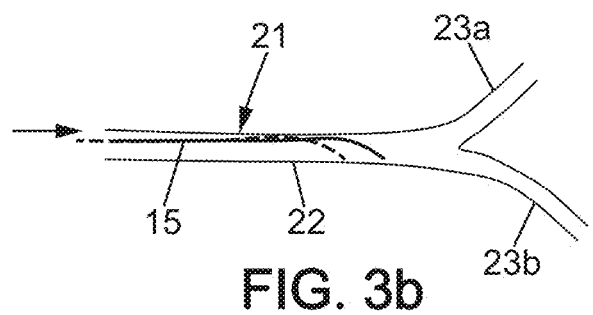
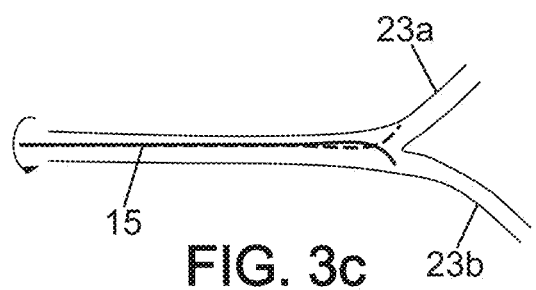

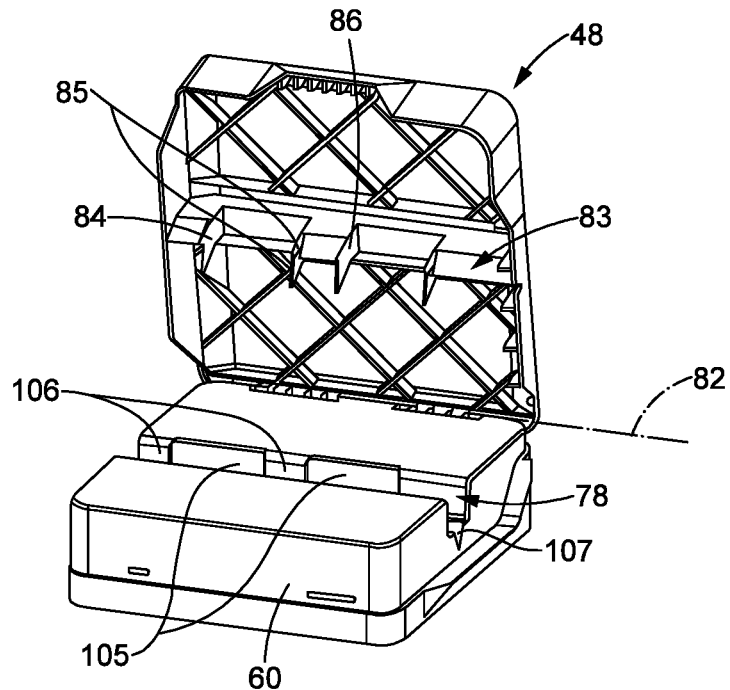
FIG. 10
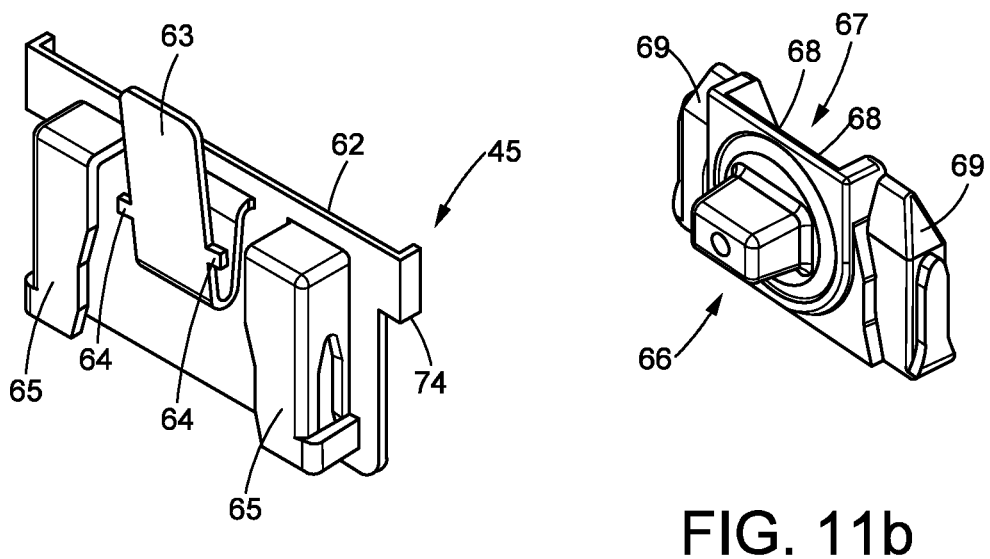
FIG. 11a
FIG. 11b

ROBOTIZED MODULE FOR GUIDING AN ELONGATE FLEXIBLE MEDICAL DEVICE

CROSS-REFERENCE TO RELATED APPLICATION

This Application is a 35 USC § 371 US National Stage filing of International Application No. PCT/FR2015/051562 filed on Jun. 12, 2015, and claims priority under the Paris Convention to French Patent Application No. 14 55330 filed on Jun. 12, 2014.

FIELD OF THE DISCLOSURE

The present invention relates to robotic modules for driving elongate flexible medical devices.

BACKGROUND OF THE DISCLOSURE

The manual insertion of a catheter or a guide into a patient is a relatively conventional surgical procedure. However, since this procedure is monitored using X-rays, the surgeon performing this procedure is subject to consequent irradiation if carrying out such an operation on a large number of patients.

In order to reduce the risks to the surgeon, attempts have been made to robotise such an insertion. This robotisation is complex because gripping the catheter is difficult. The catheter is bathed in a preservation liquid and must remain sterile. Furthermore, it is desired to control the translational and rotational movements of the catheter alternately and/or simultaneously. Reliability is a decisive criterion for these robotic systems.

A drive system has recently been proposed in U.S. Pat. No. 7,927,310 for managing the movement in both translation and rotation of the catheter. The catheter is held on a plate that can rotate relative to a base for driving the rotation. The plate itself comprises a translation drive mechanism. In addition, remote motors fixed on the frame and systems for the transfer of the movement to the catheter are used. It is preferable not to have installed motors, for reasons of power supply, space and sterility.

SUMMARY OF THE DISCLOSURE

Although this configuration is satisfactory, simplification of this type of mechanism is continuously sought, in particular with a view to increasing reliability.

To this effect, according to the invention, a robotic drive module for driving an elongate flexible medical device is provided, comprising:
a base,
a pair of drive members each having a drive surface, the pair of drive members being placeable in a drive configuration in which the drive surfaces of the drive members of the pair of drive members engage with the elongate flexible medical device to be driven and are arranged on either side thereof,
the pair of drive members being movably mounted relative to the base along one degree of freedom, between a first and second position,
a control member, suitable for controlling a movement relative to the base of the drive members of the pair of drive members in the drive configuration from the first to the second position, thus driving the elongate flexible medical device relative to the base,
a disposable consumable sterile barrier, comprising an attachment bracket for each drive member and flexible portions between two adjacent attachment brackets, the flexible portions being connected to the attachment brackets, each drive member being attached to an attachment bracket, the drive surfaces of the attachment brackets being intended to come into contact with the elongate flexible medical device.

Through these provisions, the driving of the elongate flexible medical device can be implemented in a sterile manner, even over long and complex trajectories.

In the preferred embodiments of the invention, it may also be possible to make use of one and/or the other of the following provisions:
the pair of drive members can be placed alternately in the drive configuration and in a free configuration in which the drive surface of the drive members of the pair of drive members is not engaged with the elongate flexible medical device,
the control member is suitable for controlling, in a repeated cyclical manner, the movement of the drive members relative to the base in the drive configuration from the first to the second position, and a movement relative to the base of the drive members of the pair of drive members in free configuration from the second to the first position without driving the elongate flexible medical device relative to the base;
the base is a first base, the pair of drive members is a first pair of drive members, the robotic module further comprising:
a second base,
a second pair of drive members each having a drive surface, the pair of drive members being placeable in a drive configuration in which the drive surfaces of the drive members of the pair of drive members engage with the elongate flexible medical device to be driven, and are arranged on either side thereof,
the second pair of drive members being movably mounted relative to the second base along one degree of freedom between a first and second positions,
a control member being further adapted to control a movement relative to the base of the drive members of the second pair of drive members in the drive configuration from the first to the second position, thus driving the elongate flexible medical device relative to the second base,
the second pair of drive members can be placed alternately in the drive configuration and in a free configuration in which the drive surface of the drive members of the second pair of drive members is not engaged with the elongate flexible medical device,
the control member is adapted to control, in a repeated cyclical manner, the movement of the drive members relative to the second base in the drive configuration from the first to the second position, and a movement relative to the second base of the drive members of the pair of drive members in free configuration from the second to the first position without driving the elongate flexible medical device relative to the base;
the first base and the second base are connected together or common;
the disposable consumable sterile barrier comprises an attachment bracket for each drive member of the second pair and flexible portions between two adjacent attachment brackets, the flexible portions being connected to the attachment brackets, each drive member of the second pair being attached to an attachment bracket, the drive surfaces of the attachment brackets being intended to come into contact with the elongate flexible medical device;

the sterile barrier further comprises a continuous disposable consumable film comprising an attachment portion for each drive member and flexible portions between two adjacent attachment portions, each drive member being attached to an attachment portion of the continuous film, the drive surfaces being engaged with the elongate flexible medical device by means of the continuous film;

the sterile barrier also comprises a rigid casing, each attachment bracket being assembled on the rigid casing by means of said flexible portions;

the rigid casing comprises a plurality of windows each sealingly closed by a flexible portion;

the attachment bracket is assembled on the drive member by means of frangible zones connecting the drive surface, in contact with the elongate flexible medical device, to the assembly portion on the drive member;

the sterile barrier separates the space into two sub-spaces: a sterile sub-space containing the elongate flexible medical device, and a sub-space that is not necessarily sterile in which the drive members are disposed;

the robotic drive module includes a closed housing encompassing the drive members and, where applicable, the base, and comprising an upstream port and a downstream port through which the elongate flexible medical device extends;

the housing also includes a connection member connecting each drive member to a motor outside the housing;

the housing comprises a receptacle and a lid moving relative to the receptacle between a closed configuration, where access by an operator to the elongate flexible medical device inside the housing is prohibited, and an open configuration where access by an operator to the elongate flexible medical device inside the housing is possible;

a final portion of the trajectory of the lid from its open configuration to its closed configuration is a translation movement;

in closed configuration, in the vicinity of the drive members, a large free volume is available between the lid and the receptacle, and outside of this vicinity a reduced free volume is available between the lid and the receptacle, allowing guidance there of the elongate flexible medical device;

the housing comprises a fixed base portion carrying the drive members, and a disposable consumable cassette that can be assembled and disassembled on the base portion, the cassette comprising at least the sterile barrier;

the receptacle comprises the base portion and the sterile barrier;

each attachment bracket is detachable from the respective drive member;

the robotic module further comprises a rigid carrier bearing the attachment brackets, each attachment bracket being temporarily assembled on the carrier;

the carrier further comprises a foolproof portion, preventing assembly thereof in an undesired orientation;

the carrier is disassembled from the sterile barrier;

each attachment bracket comprises a flat wall having a front face, and comprising a barrier system for limiting movement of the elongate flexible medical device, holding the elongate flexible medical device facing the front face;

each barrier of the limiting barrier system comprises alternating recesses and protrusions.

According to another feature, the invention relates to an arteriography robot comprising a container, an elongate flexible medical device at least partially contained in the container, and a robotic drive module attached to the container and capable of driving the elongate flexible medical device out of the container.

According to another feature, the invention relates to a cassette comprising a sterile barrier comprising attachment brackets each capable of being attached to a drive member of an elongate flexible medical device, and flexible portions between two adjacent attachment brackets, the flexible portions being connected to the attachment brackets, the drive surfaces of the attachment brackets being intended to come into contact with the elongate flexible medical device.

Other features and advantages of the invention will appear in the course of the following description of one of the embodiments thereof, given by way of a non-restricting example, with reference to the attached drawings.

BRIEF DESCRIPTION OF THE DRAWINGS

Regarding the drawings:

FIG. 1b is a top view of a part of FIG. 1a,

FIG. 10 is a perspective view of a cassette with lid, FIGS. 11a and 11b are perspective views of the rear of an attachment bracket and an end piece, respectively

In the various figures, the same references designate identical or similar elements.

DETAILED DESCRIPTION OF THE DISCLOSURE

Figure 1A:
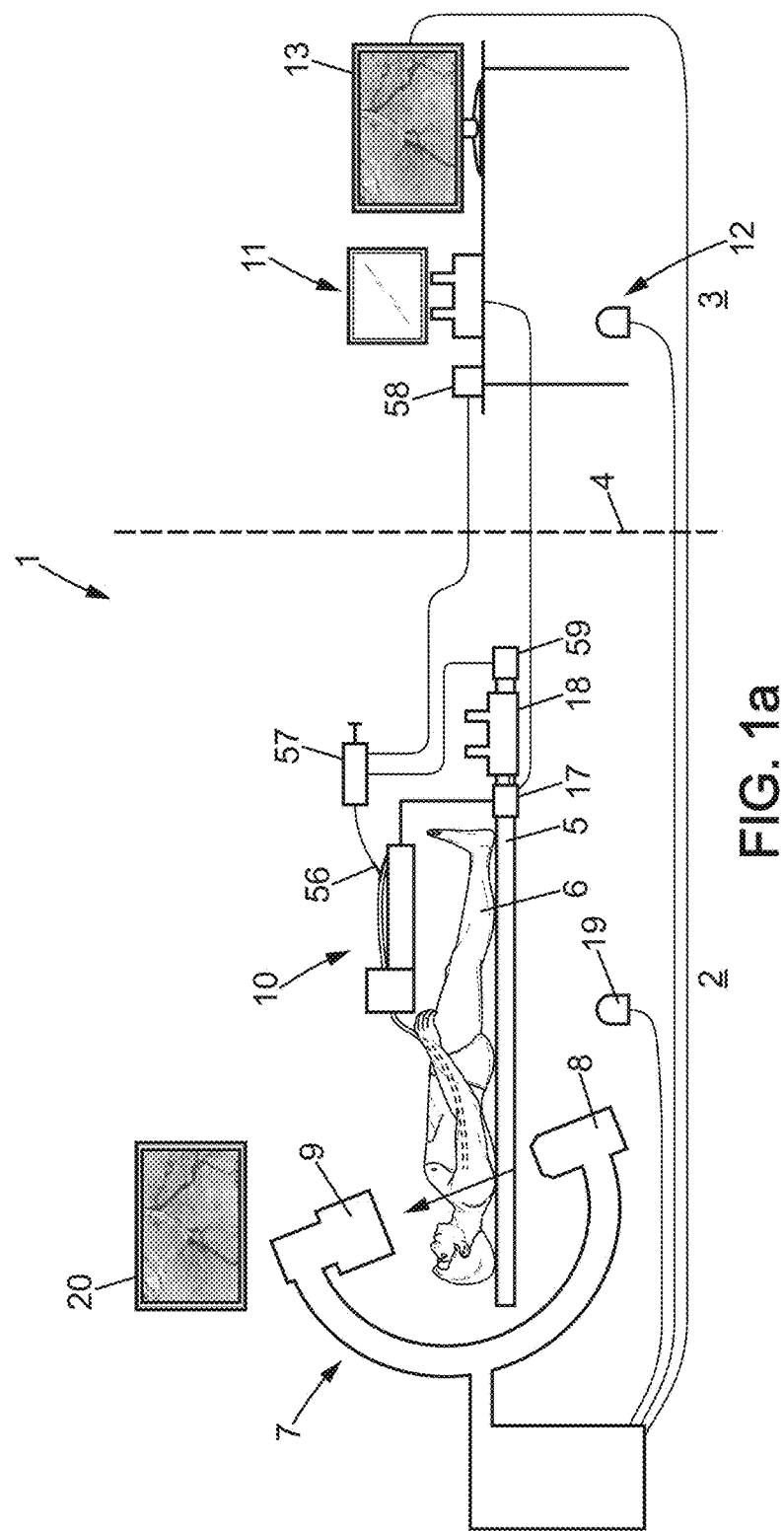
FIG. 1a is a schematic side view of a robotic arteriography facility.
Figure 1B:
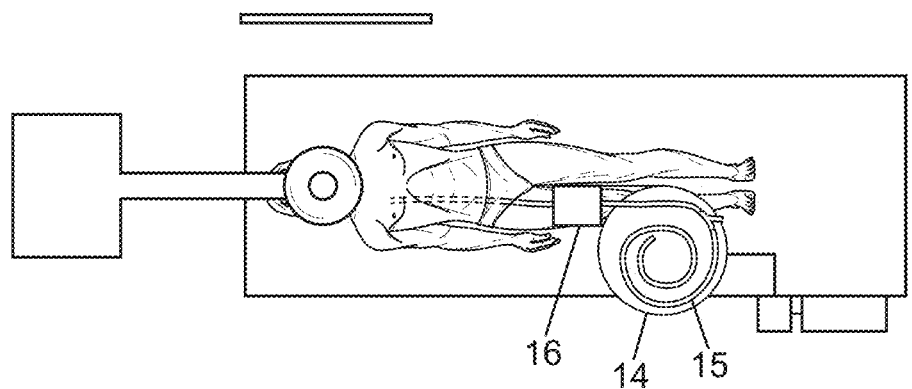

FIG. 1a schematically represents an arteriography facility 1. The arteriography facility 1 is divided into two distinct locations, an operating room 2 and a control room 3. The control room 3 can be close to the operating room 2, separated from it by a simple partition 4 opaque to X-rays, or remote. The equipment of the operating room 2 and the control room 3 are connected to one another in a functional manner, in a wired, wireless or networked manner, etc.

The operating room 2 comprises an operating table 5 for receiving a patient 6. The operating room 2 can also include a medical imager 7, in particular an X-ray imager, comprising a source 8 and a detector 9 disposed on either side of the patient, possibly able to move relative to the patient.

The arteriography facility 1 comprises a robot 10 disposed in the operating room 2.

The arteriography facility 1 comprises a control station 11 disposed in the control room 3. The control station 11 is capable of remotely controlling the robot 10. The arteriography facility 1 can also include, disposed in the control room 3, one or more remote controls 12 of the imager 7, communicating with the imager 7 in order to control the imager remotely. The arteriography facility 1 can also include a screen 13, disposed in the control room 3 and communicating with the imager 7, in order to visualise the images acquired by the imager 7 in real time in the control room 3.

The robot 10 may comprise a container 14 suitable for containing an elongate flexible medical device 15 to be introduced into the body of a patient. The elongate flexible medical device 15 may, for example, be a device to be introduced into a channel of a patient, and to be moved in said channel, in particular an artery or a vein of a patient, through a Desilet maintaining an access opening in the patient. The elongate flexible medical device can be, in particular, a catheter. Alternatively, the elongate flexible medical device can be a guide for introducing a catheter. A guide generally has a cross-sectional diameter less than that of the catheter, which is generally hollow over a portion close to the patient, or even over its entire length, so that the guide can move inside the catheter, in particular inside the body of the patient. The guide may also comprise a curved end, as will be described in more detail below.

The robot 10 may comprise a drive module 16 for driving the elongate flexible medical device 15. The drive module 16 can be controlled from the control station 11 in order to drive the elongate flexible medical device relative to the patient along at least one degree of freedom, as will be described in detail below. The drive module may comprise a communication unit 17 providing an interface with the control station 11. As needed, the robot 10 may comprise an in-room control unit 18 for controlling the robot from the operating room 2 if necessary.

It should be further noted that all the controls and feedbacks available in the control room 3 may also be available in the operating room 2 with a view to an in-room operation, such as for example a control 19 of the imager and a screen 20 for viewing the images acquired by the imager 7.

The elongate flexible medical device 15 may be connected to a connector 56 enabling injection of a contrast agent facilitating the imaging inside the elongate flexible medical device. The arteriography facility may comprise a contrast agent injector 57 connected to the connector 56, controllable by a remote control 58 disposed in the control room 3. A control 59 of the contrast agent injector may also be present in-room in the operating room 2.

Figure 2:
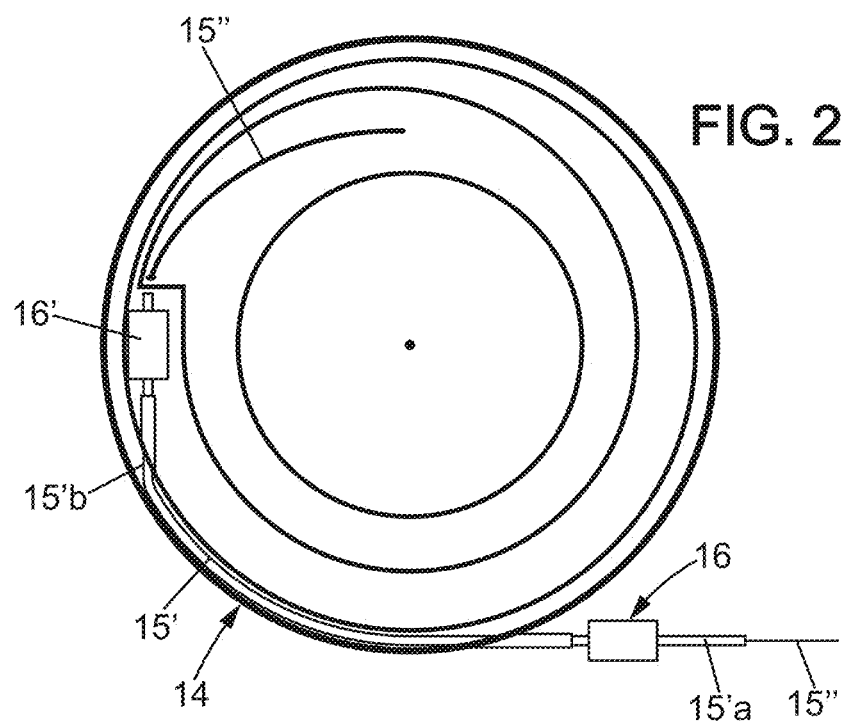
FIG. 2 is a schematic top view of a robot used in the facility of FIGS. 1a and 1b, FIGS. 3a-3c are illustrative diagrams the modes of movement of the members to be driven.

In a purely illustrative manner, FIG. 2 illustrates in more detail the container 14 receiving a catheter 15'. The container 14 maintains the catheter 15' in a suitable environment for its preservation. The drive module 16 is suitable for driving the catheter 15'. In the example, the container 14 also receives a guide 15". The container 14 maintains the guide 15" in a suitable environment for its preservation. The drive module 16' is suitable for driving the guide 15". Depending on the applications, the drive modules 16 and 16' may be identical or different. They may be in accordance with one of the embodiments presented below, if appropriate. In the present example, the guide 15" can be introduced into the catheter 15' at the rear end 15'b thereof, and extends beyond the front end 15'a of the catheter, as illustrated.

In what follows, the reference 15 will be used to alternatively designate the guide 15", the catheter 15' or, in a general way, an elongate flexible medical device medical to be introduced into the body of a patient. It may for example refer to an interventional catheter. Such an interventional catheter may have a diameter less than the catheter, so as to be coaxially guided inside the latter, inside the patient, and be hollow so as to be guided on the guide inside the patient.

FIG. 3a shows the various degrees of freedom possible with the present system. It shows the guide 15" with its front end 15"a slightly curved relative to the longitudinal main axis of the guide, and exiting from the front end 15'a of the catheter 15'. The catheter 15' may be subject to two distinct movements:

a movement in translation along its longitudinal axis,
a rotation about its longitudinal axis.

These movements can be generated in either direction.

Where applicable, the catheter 15' can be subjected to a movement combining the two simple movements described above.

Where applicable, the catheter 15' can be subjected to two movements combining the two simple movements described above, according to different combinations.

That which has been described above concerning the catheter also applies to the guide.

The guide 15" may be subject to two distinct movements:

a movement in translation along its longitudinal axis,
a rotation about its longitudinal axis.

These movements can be generated in either direction.

Where applicable, the guide 15" can be subjected to a movement combining the two simple movements described above.

Where applicable, the guide 15" can be subjected to two movements combining the two simple movements described above, according to different combinations.

In some cases the catheter itself is provided with a curved end, either to allow navigation on the same principle as a guide, or to facilitate positioning in an anatomical region having a particular curvature.

FIG. 3b shows an artery 21 of a patient, comprising a main trunk 22 and two branches 23a, 23b opening onto the main trunk. FIG. 3b illustrates the movement in translation of an elongate flexible medical device 15 (in this case a guide 15") between a retracted position represented by the dotted line and an advanced position represented by the solid line. FIG. 3c illustrates, in the same artery, a rotation of the elongate flexible medical device 15 between a first position, represented by the dotted line, where the elongate flexible medical device is ready to be moved in translation in the direction of the branch 23a, and a second position, represented by the solid line, where the elongate flexible medical device is ready to be moved in translation in the direction of the branch 23b.

The elongate flexible medical device can be driven by the drive members according to the movement(s) described above. The drive members can be arranged in pairs.

According to one embodiment, a given drive member can be actuated by an actuator.

An actuation system 55, 55', 55" is thus illustrated with a drive finger 24 in three independent spatial directions.

Figure 4:
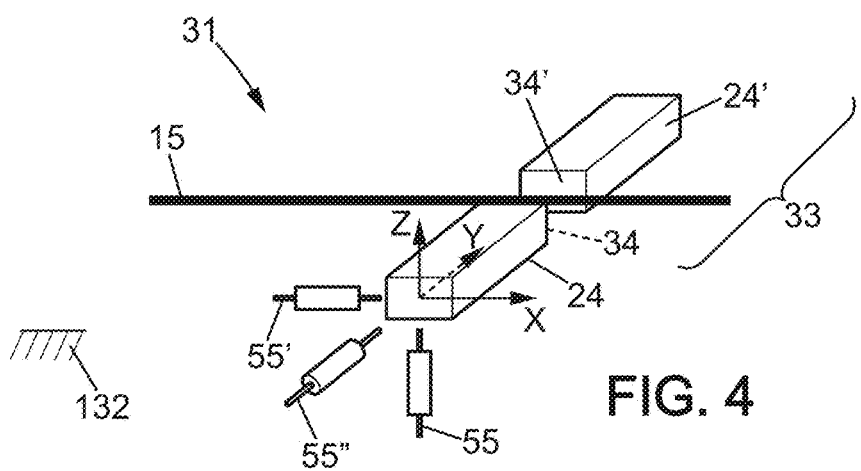
FIG. 4 is a schematic perspective view of a portion of a drive module in free configuration.

FIG. 4 illustrates a drive module 31 according to a first embodiment. Said drive module 31 is suitable for driving an elongate flexible medical device 15 extending in a longitudinal direction X. It should be noted that the longitudinal direction X at the drive module 31 is not necessarily the same as that of the elongate flexible medical device 15 at the end thereof, but that a translation and/or a rotation of the elongate flexible medical device 15 along/about the longitudinal direction X at the drive module 31 will result respectively in a translation and/or rotation of the elongate flexible medical device 15, along/about its longitudinal direction at the end thereof.

The drive module 31 comprises a base 132 and at least one drive member 24 movably mounted relative to the base 132. The drive member 24 is, for example, movably mounted relative to the base 132 with three degrees of freedom.

In the example shown, the drive module 31 further comprises a second drive member 24'. The drive member 24, also referred to in the following as the first drive member, and the second drive member 24' together form a pair of drive members 33. A pair of drive members 33 comprises two drive members which cooperate together to generate a movement of the elongate flexible medical device 15 relative to the base 132. In the example shown, the second drive member 24' is movably mounted relative to the base 132. The second drive member 24' is, for example, movably mounted relative to the base 132 with three degrees of freedom.

The first drive member 24 and the second drive member 24' are coupled for simultaneous movement. For example, the first and second drive members 24, 24' may be individually controlled independently of one another, but according to respective synchronised commands. Alternatively, a common command may be provided which will be broadcast to both the first and second drive members 24, 24' by a mechanical or electronic connection between the control systems of same.

Each drive member 24, 24' has a respective drive surface 34, 34'. The elongate flexible medical device 15 is disposed between the drive surfaces 34, 34' of the drive members 24, 24' of a given pair. To clarify the ideas, the drive surfaces 34, 34' are spaced apart in the Y direction.

The pair of drive members 24, 24' can be placed in a free configuration, illustrated in FIG. 4, wherein the drive surface 34, 34' of the drive members 24, 24' of the pair of drive members 33 is not engaged with the elongate flexible medical device 15.

The pair of drive members 33 can be placed in a drive configuration in which the drive surfaces 34, 34' of the drive members of the pair of drive members is engaged with the elongate flexible medical device 15 to be driven. The force applied by a drive member on the elongate flexible medical device in this configuration is, for example, of the order of a few Newtons (5-30 N, for example). Recall means are, for example, arranged to return the pair of drive members to the free configuration, which allows a safety function to be provided, for example in the event of an interruption to the electrical power supply.

To place the pair of drive members 33 alternately in the free and drive configurations, a relative movement of one relative to the other of the two drive members 24, 24' can be commanded. This movement may for example involve the displacement of one drive member 24 relative to the base, while the other remains fixed. Alternatively, the two drive members 24, 24' can both move toward one another relative to the base.

In the example, a displacement in the Y direction is envisaged.

In the embodiment shown, the two drive members 24, 24' are movable relative to the base along one degree of freedom. This degree of freedom differs from that allowing the alternate placement of drive members between the free and drive positions. In particular, the drive members 24, 24' can move relative to the base along one degree of freedom in the drive configuration thereof. Thus, the movement to the drive members along one degree of freedom in the drive configuration thereof, generates a movement of the elongate flexible medical device relative to the base of 132.

An example describes the generation of a movement in translation of the elongate flexible medical device in the longitudinal direction X of same.

The starting position corresponds to that of FIG. 4 described above. First, the free configuration is changed to the drive configuration. According to the example, said change is achieved by a movement of the drive members in opposite senses along the Y direction. The amplitude of this movement may depend on the elongate flexible medical device 15 to be driven. A guide, with smaller diameter than the catheter, may require a larger amplitude movement than the catheter from the same starting position.

In the drive configuration, a movement of the drive members is simultaneously generated in the same sense along the longitudinal direction X, in a first direction, which generates an identical movement of the elongate flexible medical device 15.

The drive configuration is changed to the free configuration. According to the example, said change is achieved by movement of the two drive members in opposite senses in the Y direction, in the opposite direction to the direction for switching the drive members from the free configuration to the drive configuration.

In the free configuration, a movement of the drive members is simultaneously (or otherwise) generated in the same sense along the longitudinal direction X, in a second direction opposite to the first direction, which does not generate a movement of the elongate flexible medical device 15. The system has then returned to the starting configuration.

The steps above can be repeated in a controlled cyclic manner in order to generate a translation of the elongate flexible medical device along a long course (for example of order several metres) along the longitudinal direction X in the first direction.

The displacement of the elongate flexible medical device along a long course along the longitudinal direction X in the second direction can be achieved by a series of opposing operations to the one that has just been described.

The frequency of the cycle can be adjustable and controllable. In particular, a low frequency can be used for introducing the elongate flexible medical device into the patient, or even several levels of low frequency, in order to allow, in particular, slow navigation in difficult environments. A rapid frequency can be used, for example for withdrawal, or even for an emergency withdrawal. The movement amplitudes for each cycle can also be adjustable.

For the movement in translation, speeds between 0.1 and 200 millimetres per second are possible.

An example describes the generation of a movement in rotation of the elongate flexible medical device about its longitudinal direction X.

The starting position corresponds to that of FIG. 4 described above. First, the free configuration is changed to the drive configuration. According to the example, said change is achieved by a movement of the drive members in opposite senses along the Y direction. This change is the same as that already described above.

In the drive configuration, simultaneous movement of the drive members is generated in opposite senses along a Z direction transverse to the longitudinal direction X, different from the Y direction, which generates a movement in rotation of the elongate flexible medical device 15 around the longitudinal direction X. In particular, the elongate flexible medical device rolls, preferably without sliding, on the drive surfaces 34, 34' of the drive members 24, 24'. Alternatively, it is possible to move just one of the two drive members, while the other remains fixed.

The drive configuration is changed to the free configuration. According to the example, said change is achieved by movement of the two drive members in opposite senses in the Y direction, in the opposite direction to the direction for switching the drive members from the free configuration to the drive configuration.

In the free configuration, a movement of the drive members is simultaneously (or otherwise) generated along the direction Z, opposite to the movement described above, which does not generate a movement of the elongate flexible medical device 15. The system has then returned to the starting configuration.

The steps above can be repeated in a controlled cyclic manner in order to generate a rotation of the elongate flexible medical device along a long course (for example of several times 360°) about the longitudinal direction X in the first direction of rotation.

The displacement of the elongate flexible medical device along a long course around the longitudinal direction X in the second direction of rotation, opposite to the first, can be achieved by a series of opposing operations to the one that has just been described.

In the two embodiments above, a movement sequence was described, during the course of which a movement of a drive member is expected to have been completed in one direction, in order to initiate another movement.

However, given that the actuations of drive members with various degrees of freedom can be made independent, by using the three actuation systems 55, 55', 55" described above in an independent manner, the movement could be implemented simultaneously with the movement of a drive member along two degrees of freedom. For example, the movement of the drive members between the end of the drive course and the return to the initial position could include a phase intermediate between a first pure separating phase and a second pure return phase to the initial position, in which these two movements are combined. A similar intermediate phase is also possible between the separated position at the end of the drive course and the position taken at the start of the drive course, between the pure return phase to the initial position and a pure approach phase. To set a limit, it would not be possible to have more pure return phases returning to the initial position, pure separating and pure approach phases, since there is risk of generating parasitic movements of the elongate flexible medical device.

In addition, while a purely translational movement of the elongate flexible medical device and a purely rotational movement have been described independently, these two movements could alternatively be combined. It would suffice, in the engaged configuration, to combine the suitable movements of the drive members in order to simultaneously generate translation and rotation.

The previous example comprises a single pair of drive members.

Alternatively, there can be several pairs of drive members. For example, by way of description, there could be two pairs of drive members. The drive members 24", 24''' of the second pair 33' may be similar to those of the first pair, and could in particular comprise drive surfaces 34", 34''', and be actuated from the remote control station 11, or even from the local control unit 18, according to similar implementations to those of the first pair. The first pair 33 and the second pair 33' of drive members can be offset relative to one another along the longitudinal axis X of the elongate flexible medical device. According to a first example, the two pairs 33, 33' may be coplanar in the free configuration thereof. That is to say, they can be provided opposite a base 132 common to the two pairs. Alternatively, the bases 132, 132' of each pair could be independent, or even non-coplanar.

The actuations of the two pairs may be synchronised. For example, the actuations of the two pairs can generate identical simultaneous movements of the two pairs.

Alternatively, the two pairs can be actuated in a synchronised manner to generate the offset movements in phase. That is to say, a first pair 33 can be in the drive configuration while another pair is in free configuration, and vice versa. For example, there is always at least one pair in the drive configuration. At each given moment, this could be the first pair, the second pair, or even both pairs at the same time. Such a configuration allows the holding of the elongate flexible medical device to be improved. In particular, when the elongate flexible medical device is moved by rubbing against an anatomical area of the patient, it must be possible to ensure it is sufficiently held to overcome the local resistance to the movement. This is made all the more difficult when the elongate flexible medical device is slippery, due to being held in a solution for example.

In the embodiments described above, the drive members are arranged in a symmetrical manner relative to a general median plane of the elongate flexible medical device.

However, alternatively, the drive members can be movably mounted relative to the base 132 in order to move the elongate flexible medical device locally sideways relative to its neutral longitudinal axis X'. The neutral longitudinal axis X' is defined by the longitudinal axis naturally occupied by the elongate flexible medical device without any stress applied by the drive components 24. Such a lateral offset is possible by generating a simultaneous movement of the drive members 24, 24' in the engaged configuration in the same sense along a transverse direction (Y or Z axis, or a combination along said two axes) relative to the engaged configuration on the neutral longitudinal axis.

If applicable, if several pairs of drive members are used, these can be disposed, in the engaged configuration, according of different lateral offsets relative to the neutral longitudinal axis. It is then possible to use a "crank-type" actuation.

Figure 5A:
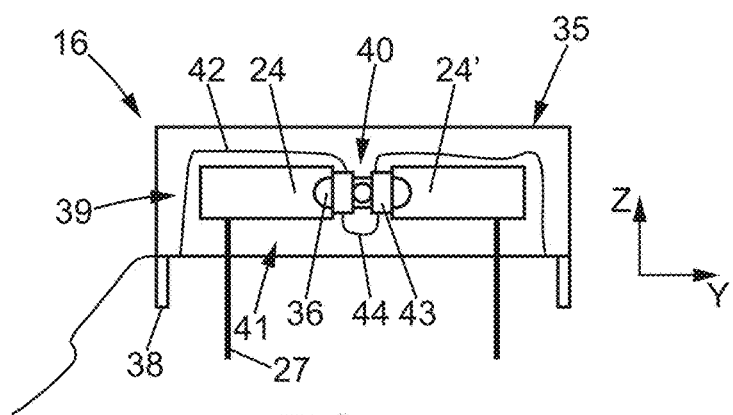
FIG. 5a is a plan view of the face of a module according to one embodiment.
Figure 5B:
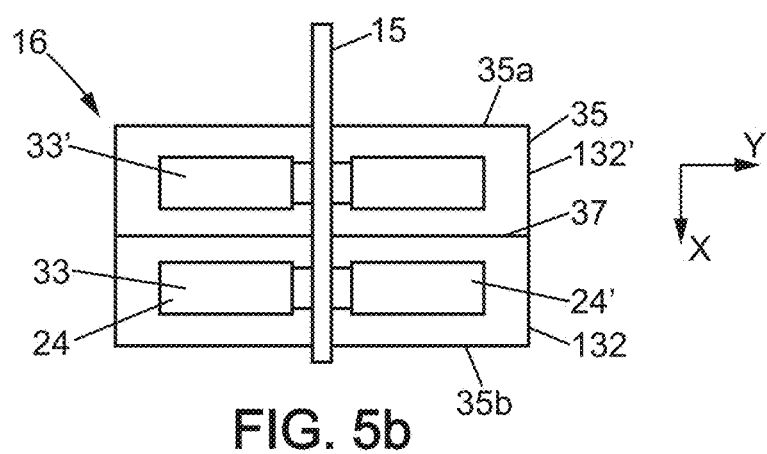
FIG. 5b is a plan view from above of the module of FIG. 5a, FIG. 6 is a similar view to FIG. 5a, without transparency, in the open configuration of the housing.

FIGS. 5a and 5b show a robotic drive module 16 comprising a housing 35 housing the drive members 24, 24', 24", 24'''. The housing 35 has openings allowing the passage of actuation rods 27 (only the actuation rod along Z is shown in FIG. 5a), the other end of which is rigidly connected to an actuator (not shown). Alternatively, it should be noted that the rod, illustrated in FIG. 5b with reference sign 27, is not necessarily an actuation rod, but may simply be a movement transfer rod, rigidly connected to one end of the drive member 24. In this case, it is the other end of said movement transfer rod which is subject to the actuation by the actuation systems, 55, 55', 55". The housing 35 also comprises an upstream face 35a and a downstream face 35b each comprising a port 36 allowing the passage of the elongate flexible medical device. The port 36 may be produced in the form of a slot to allow for the emergency withdrawal of the elongate flexible medical device.

If, according to the example shown, several pairs of drive members are used, offset with respect to one another along the longitudinal X axis, two successive pairs of drive members 33, 33' can be separated by an intermediate partition 37 of the housing. The intermediate partition 37 may also comprise a port for the passage of the elongate flexible medical device, this port being delimited by a rim that can form a support area for the elongate flexible medical device.

The housing 35 comprises an attachment system 38 for attaching the housing 35 to a support, for example rigidly attaching to the container 14. Any type of attachment is feasible, removable or otherwise, for example by clipping or electromechanical locking.

Figure 8:
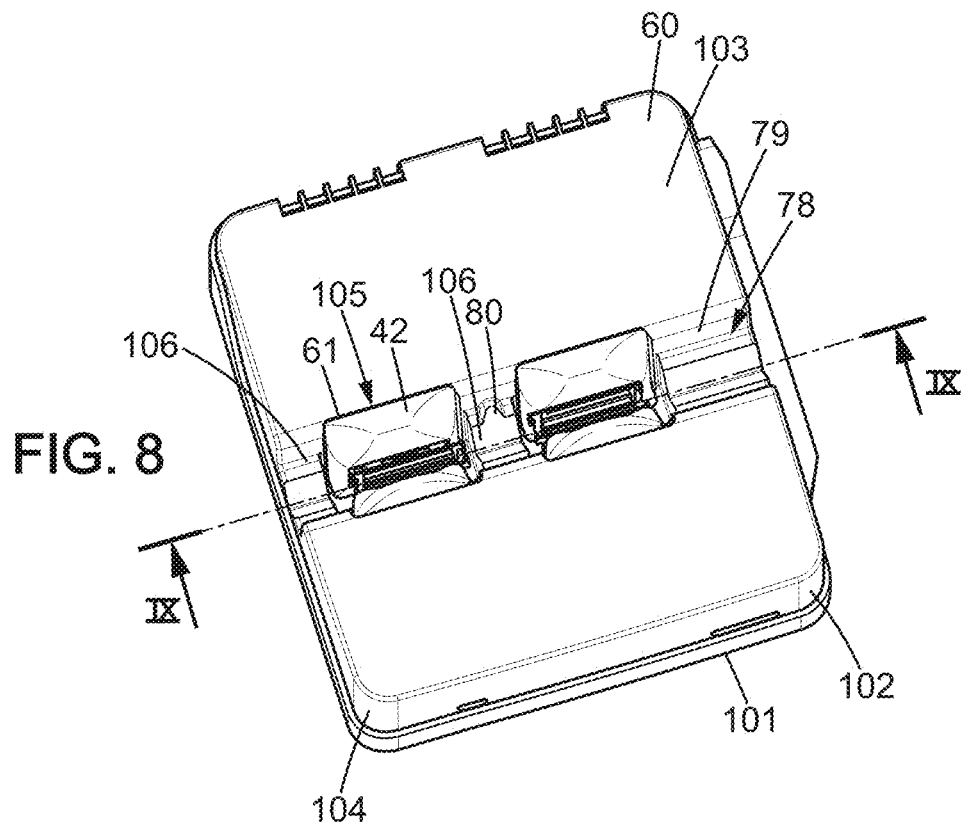
FIG. 8 is a perspective view from above of an embodiment of the cassette (without lid)

The housing 35 also comprises a sterile barrier 39 which will be described in more detail below. In particular, the housing 35 comprises a portion of the fixed base 101, and a disposable consumable cassette 102. The base portion 102 carries the drive members 24-24'''. The cassette 102 can be assembled on and disassembled from the portion of the fixed base 101 by any appropriate mechanism. As shown in FIG. 8, in one example, the cassette 102 interacts by nesting (complementarity of shape) in the portion of the fixed base 101. The cassette 102 includes the sterile barrier 39. The sterile barrier 39 can be connected to the housing 35. The sterile barrier 39 separates the space into two sub-spaces: a sterile sub-space 40 containing, in particular, the elongate flexible medical device 15, and a sub-space that is not necessarily sterile 41; In the example shown, the drive members 24, 24' are disposed in the not-necessarily-sterile sub-space 41. That is to say, the drive members 24, 24' interact with the elongate flexible medical device through the sterile barrier 39.

For example, the sterile barrier 39 comprises a continuous film 42 comprising an attachment portion 43 for each drive member 24, 24', and flexible portions 44 between two adjacent attachment portions. The flexible portions 44 are for example translucent. Each drive member 24, 24' is attached to an attachment portion 43 of the continuous film 42, the drive surfaces 34, 34' being engaged with the elongate flexible medical device 15 by means of the continuous film 42.

Figure 7:
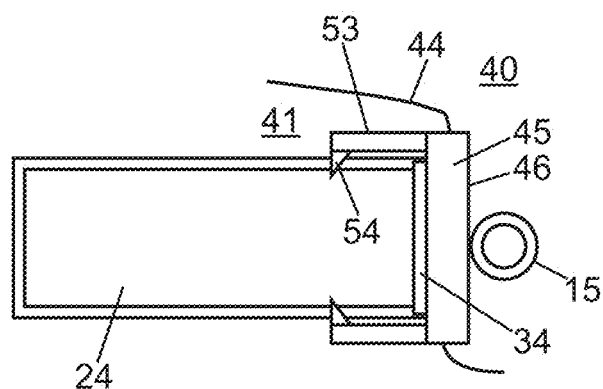
FIG. 7 is a schematic view of the face of a drive member.

As can be seen in FIG. 7, it is envisaged for example that the flexible portions 44 are connected to an attachment bracket 45. The flexible portions 44 are, for example, overmoulded onto the attachment brackets 45. The attachment bracket 45 can be assembled by any appropriate means on the drive member 24, by means of an assembly portion 54, such as for example by clipping in the not-necessarily-sterile subspace 41 (in which case the assembly portion is a clipping portion). The drive surface 46 of the attachment bracket 45, in contact with the elongate flexible medical device 15, can be specially adapted to this contact. For example, it is moulded, striated, cushioned and/or has a coating suitable for this contact.

The flexible portions 44 are sufficiently long and flexible to allow for the relative movements described above for the drive members 24, 24' without impeding or without deterioration of the sterile barrier 39.

The attachment brackets 45 may comprise frangible zones 53 such as arms connecting the drive surface 46 to the clipping portion. After an intervention, when the sterile barrier is withdrawn, the frangible zones 53 are broken. This mechanism provides a safety device for preventing, if applicable, reinstallation of a sterile barrier for use in a subsequent intervention.

According to one alternative, as shown in FIG. 8, the sterile barrier 39 has a rigid casing 60 with windows 61. There is, for example, one window 61 per drive member 24. The windows 61 are arranged, in particular, in the side walls 79 of a channel 78 of the casing, extending substantially in the X direction. Thus, the casing 60 comprises an upper wall 103, for example flat, in which the channel 78 is arranged, and a peripheral skirt 104 used to fit the casing 60 on a fixed component. The channel 68 has a region 105 with windows, in which two windows 61 are disposed facing one another, and a region 106 without windows adjacent to the region 105 with windows. In the present case where two pairs of drive members are used, the channel has two regions with windows 105, and one region without windows 106 between these regions with windows 105. The channel also has a rear region without windows 106 and a front region without window (the terms "rear" and "front" being used with reference to the patient). The channel 68 may also comprise a localised relief 80 forming a foolproof device. The dimensions of the window 61 in the X and Z directions are significantly greater than the respective course of the drive members 24 in these directions. One window 61 is described below, it being understood that the same description applies to the other windows. A flexible film 42 is connected around the perimeter of each window, and sealingly closes each window. An attachment bracket 45 extends into each window 61. The attachment bracket 45 is suspended on the casing 60 by means of the flexible film 42. The flexible film 42 is connected around the perimeter of the attachment bracket 45 in a sealing manner. The flexibility of the flexible film 42 allows a movement of the attachment bracket 45 in a certain range, in each of the three spatial directions, while maintaining the sealing of the assembly of the attachment bracket 45 to the casing 60. Thus, the attachment bracket 45 is sealingly connected to the casing 60 by the flexible portions 44.

Figure 9:
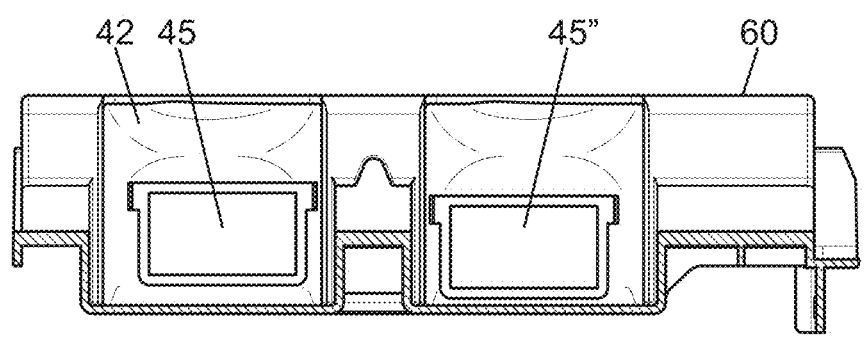
FIG. 9 is a sectional view along the line IX-IX of FIG. 8.

FIG. 9 thus illustrates the attachment brackets 45 and 45" in different positions along the X and Z axes. The attachment brackets 45 and 45" are also in different positions along the Y axis, which is not visible in this cross-sectional view. The flexibility of the flexible film 42 allows these movements.

Figure 12:
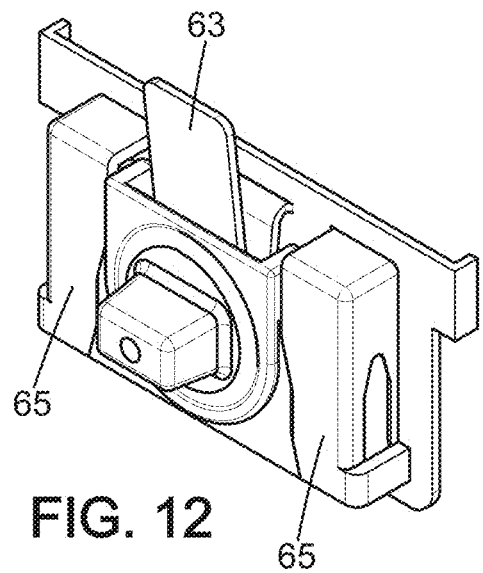
FIG. 12 is a view similar to FIG. 11a where the end piece is assembled on the attachment bracket.

FIGS. 11a, 11b and 12 show an example assembly of the attachment bracket 45 with the drive member 24. FIG. 11a illustrates the attachment bracket 45 (the flexible film 42 is not shown). The attachment bracket 45 comprises a flat wall 62 on the rear of which is mounted a system for removable assembly with the drive member. On the front of the flat wall 62 is the drive surface 46 in contact with the elongate flexible medical device ("front" and "rear" being used with reference to the elongate flexible medical device). The removable assembly system includes an elastic tab 63 bearing two locking lugs 64. The removable assembly system also comprises a guidance system. The guidance system comprises two mutually symmetrical parts disposed on either side of the elastic tab 63. Each part comprises a guiding wall 65 parallel and opposite the flat wall 62. The removable assembly system is open at the bottom in order to allow assembly from the top onto an end piece 66 of the drive member 24.

The end piece 66 is illustrated in FIG. 11b. The end piece is rigidly connected to the end of the drive member 24. The end piece comprises a front window 67 that is able to receive the elastic tab 63. Two stops 68 are arranged in the front window. Two lateral reinforcements 69 are disposed on either side of the front window 67. The lateral reinforcements 69 have shapes that complement the parts of the guidance system.

The attachment bracket 45 is assembled on the end piece 66 by sliding from the top. The reinforcement pieces 69 insert into the respective parts of the guidance system, being gripped there, and the elastic tab 63 inserts into the front window 67 by being elastically deformed. Once the assembly position is attained, the elastic tab 63 is partially released, allowing the lugs 64 to engage with the stops 68. This engagement prevents an upward movement of the attachment bracket relative to the end piece 66. The attachment bracket 45 and the end piece 66 are rigidly connected to each other.

In the above embodiment, since the flexible film 42 is flexible, it may be necessary to assemble each attachment bracket 45, one by one, on the corresponding end piece 66, which may be difficult because of the small size of the components, the sterile environment, the low amount of space available, given that it is necessary not to damage the flexible film 42.

Figure 13:
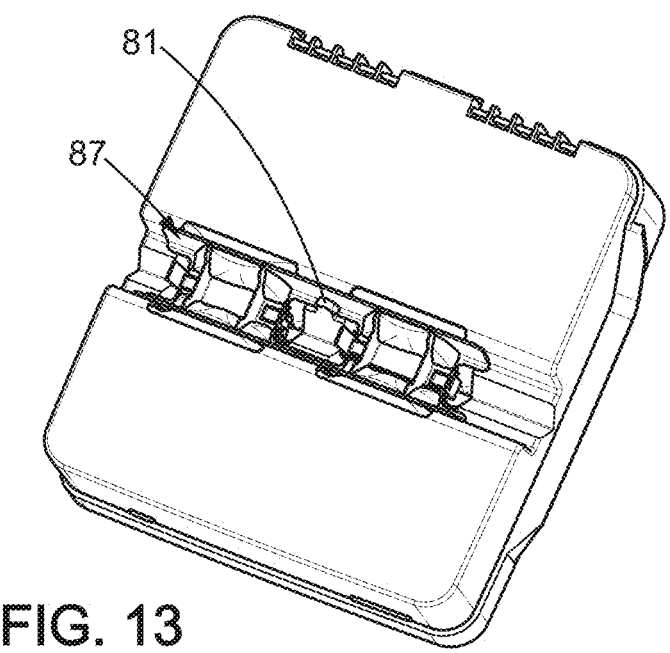
FIG. 13 is a perspective top view of the cassette incorporating a bracket carrier.
Figure 14:
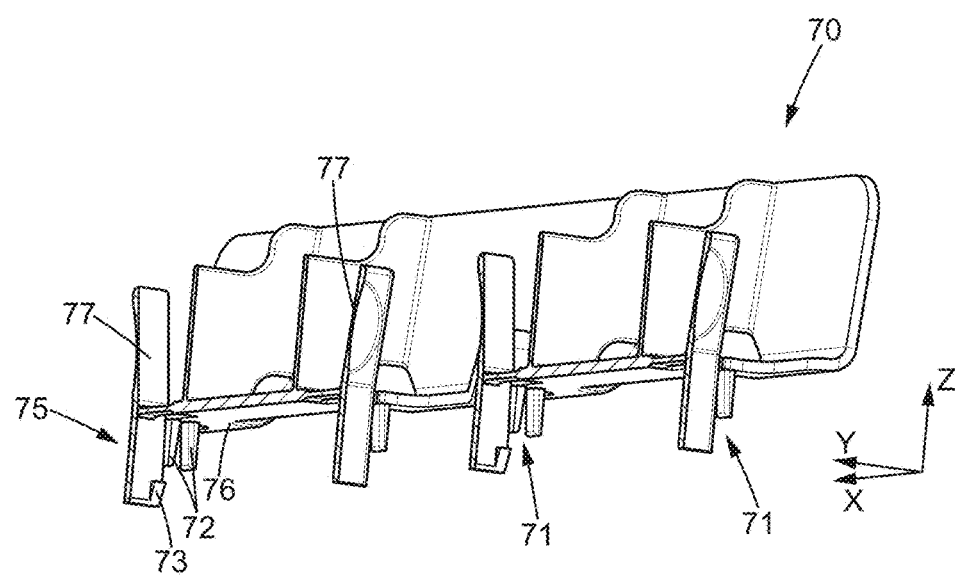
FIG. 14 is a sectional view along the section IX-IX of the bracket carrier.

In an optional alternative, a carrier 87 is provided for temporary holding of the brackets 45. According to this embodiment, the carrier uses a removable guide strip 70. The guide strip 70 is illustrated in FIG. 14, in a median cross-sectional view. The guide strip 70 has a shape generally complementing the shape of the casing 60, in particular the central channel 78 of the casing 60. It can fit into the latter in a given unique position. There is thus a localised relief 81 (FIG. 13) complementary to the relief 80 of channel 68. A bracket 45 is held by two holding regions 71 of the guide strip, the two holding regions 71 being spaced apart from one another in the X direction. The bracket 45 is held in the Y direction by the lugs 72 to be disposed either side of the flat wall 62. For example, one pair of lugs 72 is provided per holding region. A stop 73 participates in holding the bracket 45 in the Z-direction. Such a stop 73 is provided, for example, in each holding region 71. Each stop 73 engages with a complementary stop 74 arranged on the bracket 45.

The stop 73 is mounted on a flexible tab 75. Thus, the guide strip 70 comprises a base body 76 on which two flexible tabs 75 are flexibly mounted, which are able to be subjected to a certain degree of bending. The lugs 72 are disposed under the base body 75. The flexible tabs 75 comprise an actuation portion 77 accessible to a user, in order to generate a flexing of the flexible tab 75.

The bracket 45 is thus held in position between four lugs 72, while being supported at its two lateral ends by two stops 73 engaging with the stops 74. The extension of the lug 72 on the side of the rear face of the flat wall 62 is limited, so as not to interfere with the adhesion of the flexible film to the bracket 45.

The guide strip 70 is symmetrical with respect to the X-Z plane. A flexible tab 75 and bears another stop engaging with the complementary stop of the facing bracket 45.

The system that has just been described is duplicated for another pair of brackets 45 by translation along the X-axis, the two systems being produced as a single part by extension of the base body 76.

The guide strip 70 thus defines a very precise position for each of the brackets 45 with respect to the base body and, consequently, with respect to the casing 60, if there is a single mounting position of the guide strip 70 on the casing 60.

In the example shown, at rest, each of the end pieces 66 is disposed in a neutral position. This position corresponds to a position in which the end piece 66 is assembled on the bracket 45 in the position in which the bracket 45 is held by the guide strip 70 in a defined position relative to the casing 60.

In the delivery configuration, the guide strip 70 is therefore assembled on the casing 60 in the unique position, and supports the four brackets 45 in a defined position.

The actuators are at rest, so that the end pieces 66 are in a defined position.

The casing 60 is arranged in position relative to the fixed base portion 101, and the end pieces 66 and the brackets 45 are assembled together as explained above.

This assembly is possible because the guide strip 70 precisely defines the position of the bracket 45 in the space, and in particular in a position where it is in the correct location to be assembled on the respective end piece 66.

Then, by action on the actuation portions 77, the guide strip 70 is disassembled from the brackets 45 and can be withdrawn.

The brackets 45 are then mounted on the end pieces 66, being retained in a floating manner by the flexible portions 44, in a single operation.

At the end of the operation, in order to disassemble the bracket 45 from the fixed base portion 101, the elastic tab 63 is grabbed through the flexible film (which, if applicable, is translucent to facilitate this operation), and the tab 63 is pulled in order to disengage the locking lugs 64 from the stops 68. The sterile barrier can then be separated from the portion of the fixed base 101.

In variants where a different number of brackets 45 is used, a similar mechanism can be employed.

Figure 6:
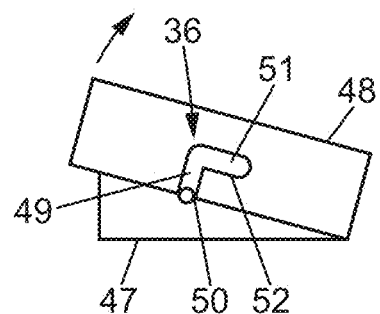

The housing 35 may comprise a receptacle 47 and a lid 48 moving relative to the receptacle 47 between a closed configuration, where access by an operator to the elongate flexible medical device 15 inside the housing is prohibited, and an open configuration where access by an operator to the elongate flexible medical device 15 inside the housing is possible. FIG. 6 illustrates an intermediate position that is possible between these configurations. The port 36 may be open to allow this placement in two distinct configurations. For example, the port 36 comprises, in an L-shape, a first branch 49 comprising an opening 50 allowing the elongate flexible medical device 15 to disengage from the lid 48, and a second branch 51 comprising a support surface 52 for the elongate flexible medical device 15 in closed configuration.

FIG. 10 shows the lid 48 according to one embodiment in a more precise manner. In this example, the lid 48 and the sterile barrier are connected and form a single consumable, the cassette 102. In this example, the lid 48 is mounted to pivot relative to the casing 60 about a pivot axis 82.

The inner face of the lid 48 comprises a guide portion 83 having a shape that partially complements that of the channel 78. In particular, in the region 106 without windows of channel 78, the guide portion 83 tends to reduce as much as possible the space 107 available for the elongate flexible medical device. More specifically, referring to FIG. 10, when the cover is in the closed configuration, the guide portion 83 and the channel 78 together define the space 107. In the region 106 without windows, the cross-section of such space 107 is similar to that of the elongate flexible medical device. On either side of the region 105 with windows, at the ends of same, the guide portion comprises forks 84. The forks 84 comprise two inclined branches 85, joining at an apex 86, in communication with the space 107 described above. The branches 85 are inclined in such a way as to guide the elongate flexible medical device, (the placement of which is freer between the portion of the guide portion 83 and the channel 78 that is disposed at the windows, as shown by the configuration of the respective portion of the guide portion 83 shown in FIG. 10), toward space 107 in the region 106 without windows.

In the above example, the lid is mounted to pivot relative to the casing around a stationary pivot axis. Alternatively, the lid could be assembled on the casing according to another motion, by means of a suitable hinge mechanism. In particular a final trajectory can be provided with a translational movement, in particular in the Z-direction, when closing the lid. Such a movement is considered safer for preventing pinching of the elongate flexible medical device between the casing and the lid during closing of the latter. In particular, a two-step closing movement can be used, an approach course into an intermediate position, then a final course as described above. The approach course can be along a different degree of freedom from the final course, for example pivoting about the X-axis, or a translation along an axis other than the Z-axis. The mechanism can involve, for example, a system of guideways guiding the movement of the lid relative to the casing along the desired trajectory.

The housing 35, where appropriate containing the drive members, can be produced as a disposable consumable. Alternatively, as explained above, a split disposable system is produced, comprising the sterile barrier, i.e. the casing, the attachment brackets 45 mounted rigidly fixed to the casing and floating by means of the flexible portions 44 of film, and possibly the lid as a disposable consumable which is assembled in a sterile sealed manner on the fixed part of the robot.

Alternatively, as shown in FIGS. 15a-15f, a removable guide strip 70 is not necessarily used as a carrier for fitting the brackets 45. In this example, the bracket-bearing carrier 87 remains fixed on the casing 60, and is also used to disassemble the brackets 45 from the end pieces 66 after use. The bracket-bearing carrier 87 comprises a mechanism 88 for removable attachment to the bracket 45. The removable attachment mechanism 88 has a stop 89 which engages with a complementary stop 90 of the bracket 45 to hold together the bracket 45 and the bracket-bearing carrier 87. The removable attachment mechanism 88 also comprises a flexible tab 91, bearing one of the stops 89, 90, allowing a detachment of the two stops, and consequently of the two components. The flexible tab 91 forms, for example, a part of the removable attachment mechanism 88.

The bracket-bearing carrier 87 also comprises a portion 92 for disengaging the bracket 45 from the end piece 66. The disengaging portion 92 can be, for example a wedge that can be inserted into the locking mechanism of the bracket 45 and the end piece 66.

Figure 15A:
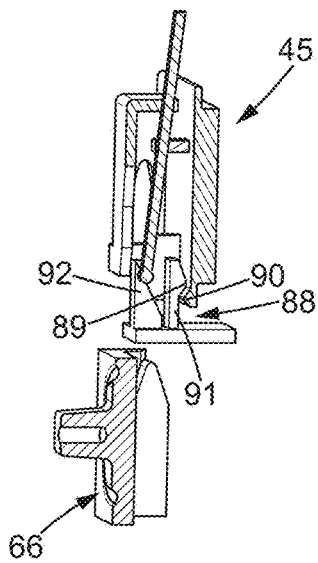
FIGS. 15a-15f are sectional views from the side which represent various stages of assembly of the bracket with the end piece according to one embodiment.

FIG. 15a also illustrates an initial position of the assembly of the casing on the fixed part of the robot, in which the bracket 45 is assembled on the bracket-bearing carrier (87).

Figure 15B:
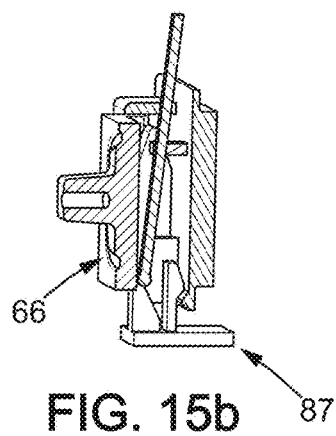
Figure 15C:
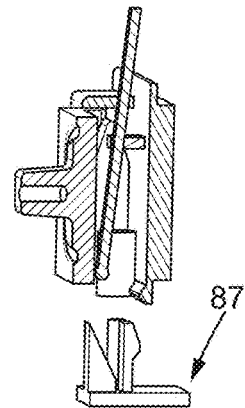

During the assembly movement, as illustrated in FIG. 15b, the bracket 45 is rigidly connected on the end piece 66 by clipping, as described previously. As illustrated in FIG. 15c, the continued movement toward the bottom of the bracket-bearing carrier 87 disengages the bracket 45, held on the end piece, from the bracket-bearing carrier 87, by elastic deformation of the flexible tab 91. The robot can then be used.

Figure 15D:
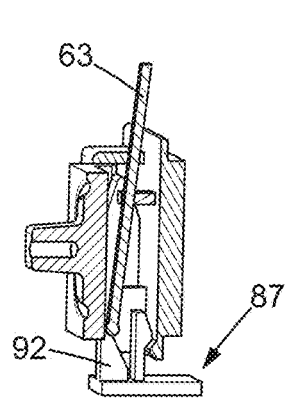
Figure 15E:
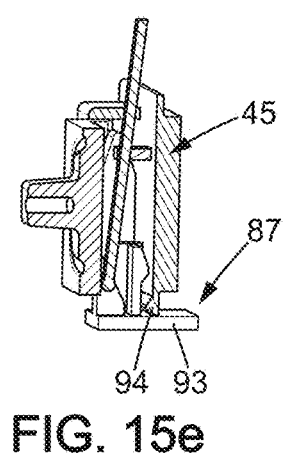
Figure 15F:
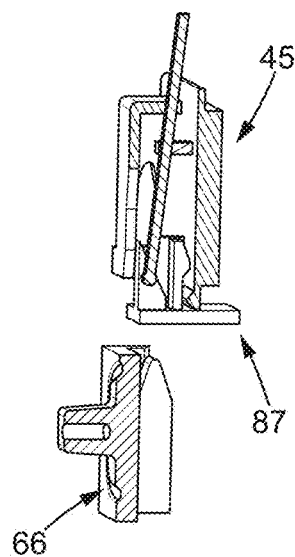

When it is desired to withdraw the bracket 45, as illustrated in FIG. 15d, an opposite movement is applied to the bracket-bearing carrier 87. The disengagement portion 92 inserts between the flexible tab 63 of the bracket 45 and the complementary portion of the end piece 66, and deflects same so as to detach the end piece 66 from the bracket 45.

The stop 89 can move beyond the stop 90 by flexing of the flexible tab 91. The continuing movement of the bracket-bearing carrier 87 drives the bracket 45 into a remote configuration of the end piece 66 (FIGS. 15e and then 15f) by bearing a support 93 of the bracket-bearing carrier 87 on a facing portion 94 of the bracket 45.

Figure 16:
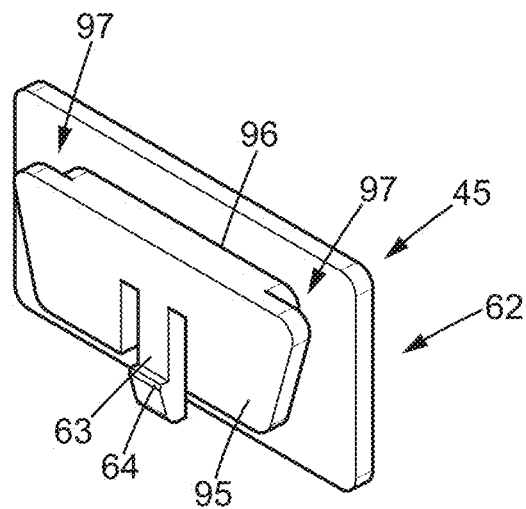
FIG. 16 is a perspective rear view which represents an embodiment of a bracket.

FIG. 16 shows another variant of the bracket 45 intended to engage with a complementary end piece 66. A rear plate 95 extends parallel to the front plate 62, an intermediate spacer 96 being disposed between the front plate 62 and the rear plate 95. The spacer 96 is shorter than the front plate 62 and rear plate 95, so as to define two guideways 97 one on either side, which guide a movement of the bracket 45 on the end piece 66. For the assembly, an elastically deformable clipping tab 63 extends downwards from the rear plate 95, and bears a lug 64.

Other removable attachment technologies than clipping may be envisaged for the bracket 45 on the end piece 66, such as a quarter-turn lock, a magnet or a solenoid.

Figure 17:
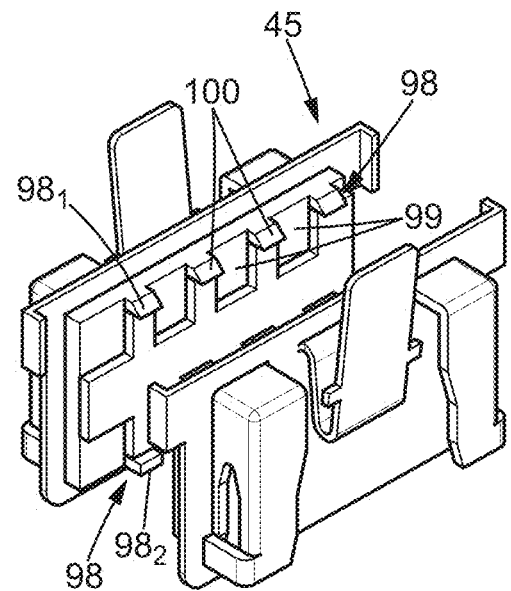
FIG. 17 is a perspective rear view representing an embodiment of an attachment bracket.

According to an embodiment, as illustrated in FIG. 17, a barrier system 98 is provided on the brackets 45. The function of the barrier system 98 is to limit any movement of the elongate flexible medical device, at a pair of brackets 45, in the Z-direction. Indeed, a looping of the elongate flexible medical device could lead to a loss of contact with the pair of brackets 45. The barrier system 98 includes, for a bracket 45, an upper barrier $98_1$ and a parallel lower barrier $98_2$. Where appropriate, each barrier $98_1$, $98_2$ of a bracket 45 is produced in the form of alternating recesses 99 and protrusions 100. Said barriers and those of the opposite bracket are produced with inverted phase, so that a recess of one corresponds to a protrusion of the other. Hence, when the two brackets 45 of a given pair are close to one another, the barriers are almost continuous. This embodiment also allows a barrier function to be produced with two identical parts placed facing one another, which facilitates the design, reduces the number of moulds, and limits the risk of installation errors.

The configuration described above facilitates the emergency withdrawal of the elongate flexible medical device 15 from the robotic module, because the elongate flexible medical device can, at any stage in the movement, be easily removed from the module by a manual manipulation.

The use of a sterile barrier between the elongate flexible medical device and the drive members is particularly well suited to the above embodiment which envisages small amplitude movements of the drive members, allowing attachment thereto of the sterile barrier and absorption of the movements by deformation of the flexible portions. However, alternatively, other embodiments are possible where the sterile barrier is disposed directly between the elongate flexible medical device and the drive members, allowing sterilisation operations, and/or the number of consumable products to be changed between two operations, to be minimised. Alternatively, for this invention, the sterile barrier could therefore be not attached to the drive members, but simply held in a suitable manner, and the drive members could be subject to large amplitude movements.

Thus, independently of the above invention, it appears that another invention relates to a robotic module for driving an elongate flexible medical device, comprising:
  a base,
  a pair of drive members each having a drive surface, the pair of drive members being placeable in a drive configuration in which the drive surfaces of the drive members of the pair of drive members engage with the elongate flexible medical device to be driven, and are arranged on either side thereof, the pair of drive members being movably mounted relative to the base along one degree of freedom, between a first and second position, a control member suitable for controlling a movement relative to the base of the drive members of the pair of drive members in the drive configuration, thus driving the elongate flexible medical device relative to the base, a continuous film, the drive surfaces engaging with the elongate flexible medical device by means of the continuous film.

The invention claimed is:

1. A robotic drive module for an elongate flexible medical device, the robotic drive module comprising:
   a base,
   a pair of drive members each having a drive surface, the pair of drive members being placeable in a drive configuration in which the drive surfaces of the drive members of the pair of drive members engage with the elongate flexible medical device to be driven, and are arranged on either side thereof, the pair of drive members being movably mounted relative to the base along one degree of freedom between a first and second position,
   a control member suitable for controlling a movement relative to the base of the drive members of the pair of drive members in the drive configuration from the first to the second position, thus driving the elongate flexible medical device relative to the base, and
   a disposable consumable sterile barrier comprising an attachment bracket for each drive member, and a flexible portion between adjacent attachment brackets, the flexible portion being connected to the attachment brackets, each drive member being attached to an attachment bracket, drive surfaces of the attachment brackets being intended to come into contact with the elongate flexible medical device,
   wherein the pair of drive members are placeable alternately in the drive configuration and in a free configuration in which the drive surfaces of the drive members of the pair of drive members is not engaged with the elongate flexible medical device,
   wherein the control member is suitable for controlling, in a repeated cyclical manner, the movement of the drive members relative to the base, in the drive configuration, from the first to the second position, and a movement relative to the base of the drive members of the pair of drive members, in free configuration, from the second to the first position without driving the elongate flexible medical device relative to the base,
   wherein each attachment bracket is assembled on the drive member by means of frangible zones connecting the drive surface, in contact with the elongate flexible medical device, to an assembly portion on the drive member.

2. The robotic module according to claim 1, wherein the base is a first base, the pair of drive members is a first pair of drive members, the robotic module further comprising:
   a second base,
   a second pair of drive members each having a drive surface, the second pair of drive members being placeable in a drive configuration in which the drive surfaces of the drive members of the second pair of drive members engage with the elongate flexible medical device to be driven and are arranged on either side thereof,
   the second pair of drive members being movably mounted relative to the second base along one degree of freedom between a first and second position,
   the control member being suitable for further controlling a movement relative to the base of the drive members of the second pair of drive members, in the drive configuration, from the first to the second position, thus driving the elongate flexible medical device relative to the second base.

3. The robotic module according to claim 2, wherein the second pair of drive members can be placed alternately in the drive configuration and in a free configuration in which the drive surface of the drive members of the second pair of drive members is not engaged with the elongate flexible medical device,
   wherein the control member is suitable for controlling, in a repeated cyclical manner, the movement of the drive members relative to the second base, in the drive configuration, from the first to the second position, and a movement relative to the second base of the drive members of the second pair of drive members, in free configuration, from the second to the first position without driving the elongate flexible medical device relative to the base.

4. The robotic drive module according to claim 2, wherein the first base and the second base are connected together or common.

5. The robotic module according to claim 2, wherein a disposable consumable sterile barrier comprises an attachment bracket for each drive member of the second pair, and flexible portions between two adjacent attachment brackets, the flexible portions being connected to the attachment brackets, each drive member of the second pair being attached to an attachment bracket, the drive surfaces of the attachment brackets being intended to come into contact with the elongate flexible medical device.

6. The robotic drive module according to claim 1, wherein the sterile barrier comprises a disposable continuous consumable film comprising an attachment portion for each drive member, and flexible portions between two adjacent attachment portions, each drive member being attached to an attachment portion of the continuous film, the drive surface being engaged with the elongate flexible medical device by means of the continuous film.

7. The robotic drive module according to claim 1, wherein the sterile barrier also comprises a rigid casing, each attachment bracket being assembled on the rigid casing by means of said flexible portions.

8. The robotic module according to claim 7, wherein the rigid casing comprises a plurality of windows each sealingly closed by a flexible portion.

9. The robotic module according to claim 1, wherein the sterile barrier separates space into two sub-spaces: a sterile sub-space containing the elongate flexible medical device, and a sub-space that is not necessarily sterile in which the drive members are disposed.

10. The robotic drive module according to claim 1, comprising a closed housing encompassing the drive members and the base and comprising an upstream port and a downstream port through which the elongate flexible medical device extends.

11. The robotic drive module according to claim 10, wherein the housing also comprises a connection member.

12. The robotic drive module according to claim 10, wherein the housing comprises a receptacle and a lid moving relative to the receptacle between a closed configuration, where access by an operator to the elongate flexible medical device inside the housing is prohibited, and an open configuration where access by an operator to the elongate flexible medical device inside the housing is possible.

13. The robotic module according to claim 12, wherein a final portion of the trajectory of the lid from its open configuration to its closed configuration is a translation movement.

14. The robotic module according to claim 12, in which receptacle includes a channel, and in which the lid includes a guide, wherein, when the lid is in the closed configuration, the guide and the channel define a space for receiving and guiding the elongate flexible medical device, the space having a greater cross-section in the vicinity of the drive members than outside of this vicinity.

15. The robotic module according to claim 10, wherein the housing comprises a remote base portion bearing the drive members, and a disposable consumable cassette, that can be assembled on and disassembled from the base portion, the cassette comprising at least the sterile barrier.

16. The robotic module according to claim 14, wherein the housing further comprises a remote base portion bearing the drive members, and a disposable consumable cassette, that can be assembled on and disassembled from the base portion, the cassette comprising at least a portion of the sterile barrier, and wherein the receptacle comprises the base portion and another portion of the sterile barrier.

17. The robotic module according to claim 1, wherein each attachment bracket can be detached from a respective drive member.

18. The robotic module according to claim 1, further comprising a rigid attachment-bracket-bearing carrier, each attachment bracket being temporarily assembled on the rigid attachment-bracket-bearing carrier.

19. The robotic module according to claim 18, wherein the rigid attachment-bracket-bearing carrier further comprises a foolproof portion preventing assembly thereof in an undesired orientation.

20. The robotic module according to claim 18, wherein the rigid attachment-bracket-bearing carrier is disassembled from the sterile barrier.

21. The robotic module according to claim 1, wherein each attachment bracket comprises a flat wall having a front face, and comprising a barrier system for limiting movement of the elongate flexible medical device, holding the elongate flexible medical device facing the front face.

22. The robotic module according to claim 21, wherein each barrier of the limiting barrier system comprises alternate recesses and protrusions.

23. An arteriography robot comprising a container, an elongate flexible medical device at least partially contained in the container, a robotic drive module according to claim 1 attached to the container, and suitable for driving the elongate flexible medical device outside the container.

24. The robotic module according to claim 1, wherein the flexible portions being connected with the attachment brackets are respectively immobile with respect to the attachment brackets to which they are connected, the attachment brackets being connected with the flexible portions are respectively immobile with respect to the flexible portions to which they are connected.

25. The robotic module according to claim 1, wherein the drive surfaces of the attachment brackets being intended to come directly into contact with the elongate flexible medical device.

* * * * *